United States Patent [19]

Nakano et al.

[11] Patent Number: 4,658,049

[45] Date of Patent: Apr. 14, 1987

[54] CARBOXYL GROUP-CONTAINING SILOXANE COMPOUND

[75] Inventors: Takaharu Nakano, Yokosukashi; Nobumasa Ohtake, Yokohamashi, both of Japan

[73] Assignee: Chisso Corporation, Osaka, Japan

[21] Appl. No.: 808,052

[22] Filed: Dec. 12, 1985

[30] Foreign Application Priority Data

Dec. 22, 1984 [JP] Japan .................... 59-271506

[51] Int. Cl.$^4$ .................................. C07F 7/08
[52] U.S. Cl. ........................................ 556/437
[58] Field of Search ............................ 556/437

[56] References Cited

U.S. PATENT DOCUMENTS

| | | | |
|---|---|---|---|
| 3,402,192 | 9/1968 | Haluska | 556/437 |
| 3,427,271 | 2/1969 | McKellar | 556/437 X |
| 3,560,544 | 2/1971 | Haluska | 556/437 |
| 3,637,783 | 1/1972 | Haluska | 556/437 |
| 3,715,377 | 2/1973 | Siciliano | 556/437 X |

*Primary Examiner*—Paul F. Shaver

*Attorney, Agent, or Firm*—Fred Philpitt

[57] ABSTRACT

A novel carboxyl group-containing siloxane compound, whether its molecular weight is low or high, having a superior heat stability, and useful as emulsifying agent, surface modifier for inorganic materials, etc. is provided, which compound is expressed by the general formula

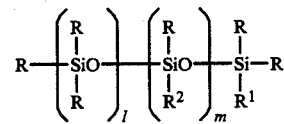

wherein R represents an alkyl group of 1 to 4 carbon atoms; $R^1$ represents R or $R^2$; $R^2$ represents $CH_2CH_2CH_2$-$(OCH_2CH_2)_n$-$COOH$; n is an integer of 1 or more; l is an integer of 0 or more; m is an integer of 0 or more; l+m is an integer of 1 or more; and $R^1$ represents $R^2$ in the case of m=0.

5 Claims, No Drawings

CARBOXYL GROUP-CONTAINING SILOXANE COMPOUND

BACKGROUND OF THE INVENTION

This invention relates to a carboxyl group-containing siloxane compound.

In general, carboxyl group-containing siloxane compounds are useful for a number of use applications where e.g. organosiloxane compounds soluble in water or alcohols are desired. The above carboxyl group-containing siloxane compounds are useful e.g. as an emulsifying agent for forming usual aqueous emulsions of organosiloxane polymers or in their applications upon e.g. alcohol-based cosmetics. Further, as to the compounds it is possible to expect their strong adhesion onto inorganic materials and modify the surface of the materials to impart to the surface, functions such as water repellency, stain resistance, non-adhesive properties, heat resistance, abrasion resistance, etc. For example, as disclosed in Japanese patent application laid-open Nos. Sho 53-10882/1978 or Sho 57-10145/1982, the compounds have been used as an ink-repelling material for litho printing. As described above, carboxyl group-containing siloxane compounds are useful as an emulsifying agent or a surface modifier for inorganic materials.

The state where carboxyl group is bonded in conventional carboxyl group-containing siloxane compounds is expressed by the general formula

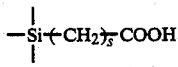

wherein s is an integer of 2 to 4, as described in Japanese patent publication Nos. Sho 40-20279/1965, Sho 41-236/1966, Sho 42-6519/1967, Sho 49-4840/1974, etc. The present inventors, however, have found that such conventional carboxyl group-containing siloxane compounds are stable to heat in the case where they have a number average molecular weight ($\overline{Mn}$) greater than 1,000, but they are decomposed by heat in the case of $\overline{Mn}$ of 1,000 or less, and have made intensive research on a manner of having carboxyl group bonded to Si atom. As a result we have found that when a polyoxyethylene chain is bonded by the medium of a bifunctional molecule, the above compounds are stable to heat even in the case of low molecular weight.

As seen from the foregoing, the object of the present invention is to provide a carboxyl group-containing siloxane compound, whether its molecular weight is low or high, having a superior heat stability, and useful as emulsifying agent, surface modifier for inorganic materials, etc.

SUMMARY OF THE INVENTION

The present invention resides in a carboxyl group-containing siloxane compound expressed by the general formula (I)

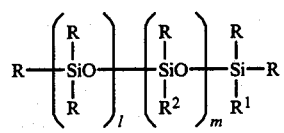

wherein R represents an alkyl group of 1 to 4 carbon atoms; $R^1$ represents R or $R^2$; $R^2$ represents $CH_2CH_2CH_2(OCH_2CH_2)_{\overline{n}}COOH$; n is an integer of 1 or more; l is an integer of 0 or more; m is an integer of 0 or more; l+m is an integer of 1 or more; and $R^1$ represents $R^2$ in the case of m=0.

DETAILED DESCRIPTION OF THE INVENTION

In the above general formula, n has no particular upper limit and may be e.g. several thousands or several ten thousands. m and l also each have no particular upper limit and may be e.g. several millions or several ten millions.

For example, a compound (II) shown below causes a ring closure reaction at about 150° C. to thereby decompose into a substance having an unknown structure, whereas a compound (III) shown below having one oxyethylene group added to the compound (II) is stable enough to effect distillation under 150° C./1 mmHg.

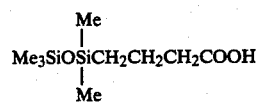

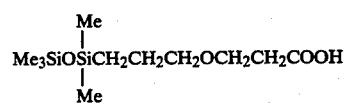

(wherein Me represents methyl group; hereinafter it has the same meaning).

The carboxyl group-containing compound of the present invention may be prepared by subjecting an ester compound (IV) shown below and a Si-H-containing siloxane compound to hydrosilylation followed by subjecting the resulting ester to hydrolysis reaction:

wherein $R^3$ may be e.g. Me (IVa), Et (this symbol represents ethyl group; hereinafter it has the same meaning) (IVb) or $SiMe_3$ (IVc). The ester compound in the case of n=1 (IVa,IVb) can be easily obtained by subjecting allyl alcohol to addition reaction to acrylonitrile in the presence of a basic catalyst (see Ind. Eng. Chem., 44, 2867 (1952)), followed by subjecting the nitrile group of the resulting product to alcoholysis. When methanol is used as a solvent in the alcoholysis, the methyl ester (IVa) can be obtained, while when ethanol is used, the ethyl ester (IVb) can be obtained (see Org. Synth., 1, 270 (1941)). Further, when the ester compounds obtained by the above reactions are further hydrolyzed in the presence of a basic catalyst to obtain the corresponding carboxylic acid, followed by reacting this acid with hexamethyldisilazane, it is possible to obtain the above trimethylsilyl ester compound (IVc) (see J. Org. Chem., 40, 1610 (1975)).

Further, in the above ester compound (IV), those of n=2 or more can be prepared by similarly carrying out the above reaction using in place of allyl alcohol, the following compound (V) shown below, prepared by subjecting a necessary number of mols of ethylene oxide to addition reaction to allyl alcohol:

$$CH_2=CHCH_2-OCH_2CH_2)_nOH \quad (V)$$

Next, a concrete example of the carboxyl group-containing siloxane compound of the present invention is as follows:

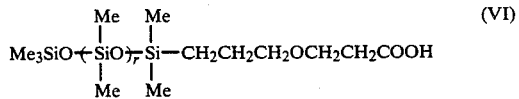
(VI)

wherein r represents an integer of 0 or more.

The above compound (VI) is readily obtained with a good yield, by subjecting a readily commercially available siloxane compound containing H atom at its one end, in the case of r=0, or a siloxane compound containing H atom at its one end obtained by reacting lithium trimethylsilanolate with hexamethylcyclotrisiloxane (see Polym. Preprints 10 (2), 1361 (1969)), in the case of r≧1, to addition reaction to the above trimethylsilyl ester compound (IVc) in the presence of a catalyst for addition reaction, preferably in N₂ gas atmosphere, followed by subjecting the resulting product to detrimethylsilylation with an alcohol.

As to the above siloxane compound containing H atom at its one end, it is possible to optionally prepare a siloxane compound having a controlled molecular weight and molecular weight distribution, as far as its average molecular weight is about 10,000 or lower. As to the reaction mol ratio of the siloxane compound having H atom at its one end to the trimethylsilyl ester compound (IVc), it is suitable to use the ester compound (IVc) in at least an equimolecular quantity to that of the siloxane compound, preferably in 1.2 times one mol of the latter. The reaction temperature is suitable to be in the range of 40° to 200° C., preferably 80° to 130° C. As for the above catalyst for addition reaction, complex compounds of metal elements belonging to group 8 of the Periodic Table may be exemplified, which include e.g. platinum compounds, rhodium compounds or paladium compounds such as known alcohol compounds, aldehyde compounds or the like of chloroplatinic acid, complexes of chloroplatinic acid with various olefins, etc.

The above alcohol used for detrimethylsilylation is preferably methanol or ethanol. The following carboxyl group-containing siloxane compounds (VII) and (VIII) can be easily prepared by similarly reacting the corresponding SiH-containing compound with the trimethylsilyl ester (IVc).

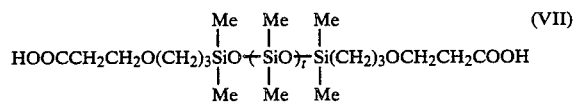
(VII)

wherein t represents an integer of 0 or more.

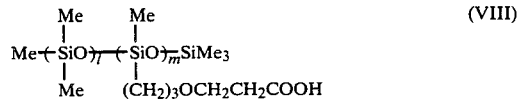
(VIII)

(In case of this example m represents an integer of 1 or more.)

The compound of the present invention is useful for various use applications, for example as an emulsifying agent for forming aqueous emulsions of usual organosiloxane polymers, as an ingredient for alcohol-based cosmetics, or as a surface modifier for imparting to the surface of inorganic materials, functions such as water repellency, stain resistance, non-adhesive properties, heat resistance, abrasion resistance, etc.

The present invention will be described in more detail by way of the following Examples, but it should not be construed to be limited thereto.

REFERENCE EXAMPLE (1) Allyl alcohol (150 g, 2.58 mols) and an ion exchange resin (IRA-400, trade name of a strongly basic anion exchange resin made by Rohm & Haas Company, U.S.A.) (25 g) were fed into a flask in N₂ current and the temperature was kept at 45° C., followed by dropwise adding acrylonitrile (125 g, 2.35 mols) over about 1 to 2 hours, thereafter agitating the mixture at 45° C. for about 8 to 9 hours, filtering off the resin and carrying out vacuum distrillation to obtain cyanoethyl allyl ether (196 g, 93°~96° C./20 mmHg). Yield: 75%.

(2) Ethanol (350 ml), water (34.4 ml) and conc. sulfuric acid (200 ml) were fed into a flask, followed by dropwise adding cyanoethyl allyl ether (222 g, 2 mols) at room temperature over 30 minutes, thereafter agitating the mixture at a reaction temperature of 100°~110° C. for about 7 hours, pouring the reaction fluid into water, extracting it with isopropyl ether, washing the extract solution with 5% NaHCO₃ aqueous solution till the extract solution became neutral, drying over MgSO₄, and subjecting the extract solution to vacuum distillation to obtain 2-allyloxypropionic acid ethyl ester (147.2 g, 94° C./18 mmHg). Yield: 46%.

(3) 2-Allyloxypropionic acid ethyl ester (147.2 g, 0.93 mol), water (300 ml) and NaOH (44.7 g) were fed into a flask, followed by agitating the mixture for about 5 to 6 hours while the reaction temperature was kept at about 60° C., thereafter dropwise adding conc. hydrochloric acid (90 ml) under ice cooling, extracting the resulting deposited oily substance with isopropyl ether, drying over MgSO₄ and carrying out vacuum distillation to obtain 2-allyloxypropionic acid (95.7 g, 108° C./5 mmHg). Yield: 79%.

The thus obtained 2-allyloxypropionic acid (170.2 g, 1.31 mol) was fed into a flask, followed by dropwise adding hexamethyldisiloxane (128.8 g, 0.8 mol) in N₂ current at room temperature over one hour, thereafter raising the reaction temperature to 80° C., then agitating the mixture for about 3 hours, and carrying out vacuum distillation to obtain 2-allyloxypropionic acid trimethylsilyl ester (IVc) (231.4 g). Yield: 87.5%.

EXAMPLE 1

2-Allyloxypropionic acid trimethylsilyl ester (65.5 g, 0.32 mol) obtained in the above Reference example, and a solution of chloroplatinic acid in isopropanol (0.042 mol; chloroplatinic acid 1 g/20 ml) were fed into a flask in N₂ current, followed by raising the temperature to 100° C., thereafter dropwise adding pentamethyldisiloxane (40 g, 0.27 mol) with stirring over 30 minutes, then further carrying out reaction at 100° C. for 2 hours, and subjecting the resulting reaction mixture solution to vacuum distillation to obtain a colorless, transparent liquid having a b.p. of 120° C./1 mmHg (77.9 g, yield 82.4%). This product was confirmed to be a silicon compound having the following structural formula, from the following analytical results:

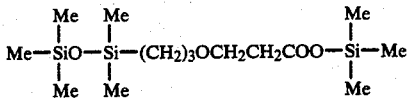

H—NMR(C₂H₄): δ 0.06 (Si—CH₃, s, 15H); 0.3(—CO₂SiMe₃, s, 9H); 0.56(—CH₂—Si, m, 2H); 1.56(—CH₂—, m, 2H); 2.5(—CH₂—, t, 2H, J=6 Hz); 3.3(—CH₂—, t, 2H, J=6 Hz); 3.6(—CH₂—, t, 2H, J=6 Hz).

IR(KBr): νmax 2960cm⁻¹(C—H); 1740cm⁻¹(C=O); 1120~1050cm⁻¹(Si—O).

MSm/e: 350(M+).

Next, the thus obtained compound (77.9 g, 0.23 mol) and methanol (100 ml) were fed into a flask, followed by agitating the mixture at room temperature for about 2~3 hours and subjecting the resulting reaction fluid to vacuum distillation to obtain a colorless, transparent liquid having a b.p. of 150° C./1 mmHg (61 g, yield: quantitative). This product was confirmed to be an oxyethylenecarboxylic acid-modified compound having the following structural formula, from the following analytical results.

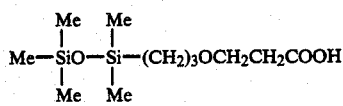

H—NMR(C₂Cl₄): δ 0.06(Si—CH₃, s, 15H); 0.56(—CH₂—Si, m, 2H); 1.6(—CH₂—, m, 2H); 2.5(—CH₂—, t, 2H, J=6 Hz); 3.3(—CH₂—, t, 2H, J=6 Hz); 3.6(—CH₂—, t, 2H, J=6 Hz); 11.6(—CO₂H, s, 1H).

IR(KBr): νmax 3050(CO₂H); 2960cm⁻¹ (C—H); 1740cm⁻¹ (C=O); 1120~1050cm⁻¹ (Si—O).

MSm/e: 278(M+).

This product was stable without causing any ring closure reaction in the vicinity of 150° C.

EXAMPLE 2

2-Allyloxypropionic acid trimethylsilyl ester (40.2 g, 0.2 mol) was reacted with a siloxane polymer containing H atom at both the ends thereof (M̄n 1,100, H equivalent 547) in the same manner as in Example 1, followed by distilling off unreacted raw materials and a low boiling substance from the reaction mixture fluid under a reduced pressure (150° C./1 mmHg) for 2 hours, and washing the residual fluid with water till the residual fluid became neutral to obtain a colorless, transparent liquid (111.6 g). This product was confirmed to be an oxyethylenecarboxylic acid-modified silicone having the following structural formula, from the following analytical results:

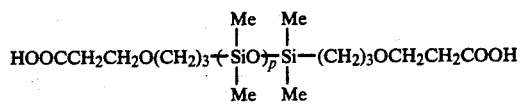

IR(KBR): νmax 3100(CO₂H); 3000~2950(C—H); 1740(C=O); 1125~1060(Si—O).

Carboxylic acid equivalent: 672 (theoretical value 677)

M̄n: 1344 (calculated from carboxylic acid equivalent) Side chain signals were confirmed according to H-NMR:

δ 0.56(—CH₂—Si, m, 2H); 1.6(—CH₂—, m, 2H); 2.5(—CH₂—, t, 2H, J=6 Hz); 3.3(—CH₂—, t, 2H, J=6 Hz); 3.3(—CH₂—, t, 2H, J=6 Hz).

EXAMPLE 3

Reaction was carried out in the same manner as in Example 2 except that the above siloxane polymer containing H atom at both the ends thereof was replaced by a siloxane polymer containing pendant type H atom (41.9 g, M̄n 5300, H equivalent 252) to obtain a colorless, transparent liquid (61.6 g). This product was confirmed to be an oxyethylenecarboxylic acid-modified silicone having the following structural formula, from the following analytical results:

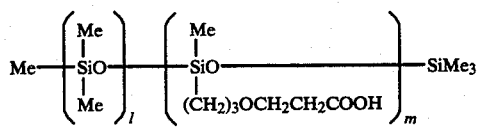

IR(KBr): νmax 3110(CO²H); 3000~2950(C—H); 1740(C=O); 1125~1050(Si—O).

Carboxylic acid equivalent: 390 (theoretical value 382).

M̄n: ≈7800 (calculated from GPC).

l̄: ≈55, m̄:≈20 (calculated from GPC, H equivalent and infrared absorption spectra).

Side chain signals were confirmed according to H-NMR:

δ 0.56 (—CH₂—Si, m, 2H); 1.6 (—CH₂—, m, 2H); 2.5 (—CH₂—, t, 2H, J=6 Hz); 3.3 (—CH₂—, t, 2H, J=6 Hz); 3.3 (—CH₂—, t, 2H, J=6 Hz).

What we claim is:

1. A carboxyl group-containing siloxane compound expressed by the general formula

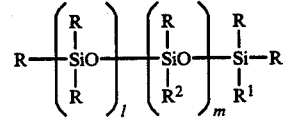

wherein R represents an alkyl group of 1 to 4 carbon atoms; R¹ represents R or R²; R² represents CH₂CH₂CH₂—(OCH₂CH₂)ₙCOOH; n is an integer of 1 to several ten thousands, l is an integer of from 0 to 134; m is an integer of from 0 to 20; l+m is an integer of from 1 to 134; and R¹ represents R² when m=0.

2. A compound according to claim 1 wherein said n is an integer of 1 to 10,000.

3. A compound according to claim 1 wherein said n is an integer of 1 to 1,000.

4. A compound according to claim 1 having a number average molecular weight of 7,800 or less.

5. A compound according to claim 1 having a number average molecular weight of 1,000 or less.

* * * * *